United States Patent [19]
Bailey et al.

[11] Patent Number: 5,122,544
[45] Date of Patent: Jun. 16, 1992

[54] PROCESS FOR PRODUCING IMPROVED SUPERABSORBENT POLYMER AGGREGATES FROM FINES

[75] Inventors: Kristy M. Bailey, Naperville; Jeffrey R. Cramm, Winfield; Mark R. Miner, Hinsdale, all of Ill.

[73] Assignee: Nalco Chemical Company, Naperville, Ill.

[21] Appl. No.: 787,699

[22] Filed: Nov. 1, 1991

Related U.S. Application Data

[63] Continuation of Ser. No. 203,368, May 31, 1988, abandoned.

[51] Int. Cl.⁵ .............................................. C08J 11/04
[52] U.S. Cl. .................................... 521/40.5; 521/40; 525/329.7; 525/385; 528/494; 528/502; 526/930; 264/37
[58] Field of Search ............... 525/329.7, 385; 521/40, 521/40.5; 528/494, 502

[56] References Cited

U.S. PATENT DOCUMENTS

| | | | |
|---|---|---|---|
| 4,123,397 | 10/1978 | Jones | 260/17.4 |
| 4,340,706 | 7/1982 | Obayashi et al. | 526/207 |
| 4,401,795 | 8/1983 | Herman et al. | 526/930 X |
| 4,654,039 | 3/1987 | Brandt et al. | 521/149 X |
| 4,698,404 | 10/1987 | Cramm et al. | 526/204 |

FOREIGN PATENT DOCUMENTS 0255814 12/1985 Japan .................................. 525/329.7

OTHER PUBLICATIONS

Translation of Japanese Kokai Application No. 55-119942 to Oobayashi, published Mar. 13, 1982.

Primary Examiner—Fred Teskin
Attorney, Agent, or Firm—Robert A. Miller; Donald G. Epple

[57] ABSTRACT

Improved water absorbent polymers can be prepared by agglomerating acrylic acid gel polymer fines with small quantities of difunctional epoxides.

3 Claims, 1 Drawing Sheet

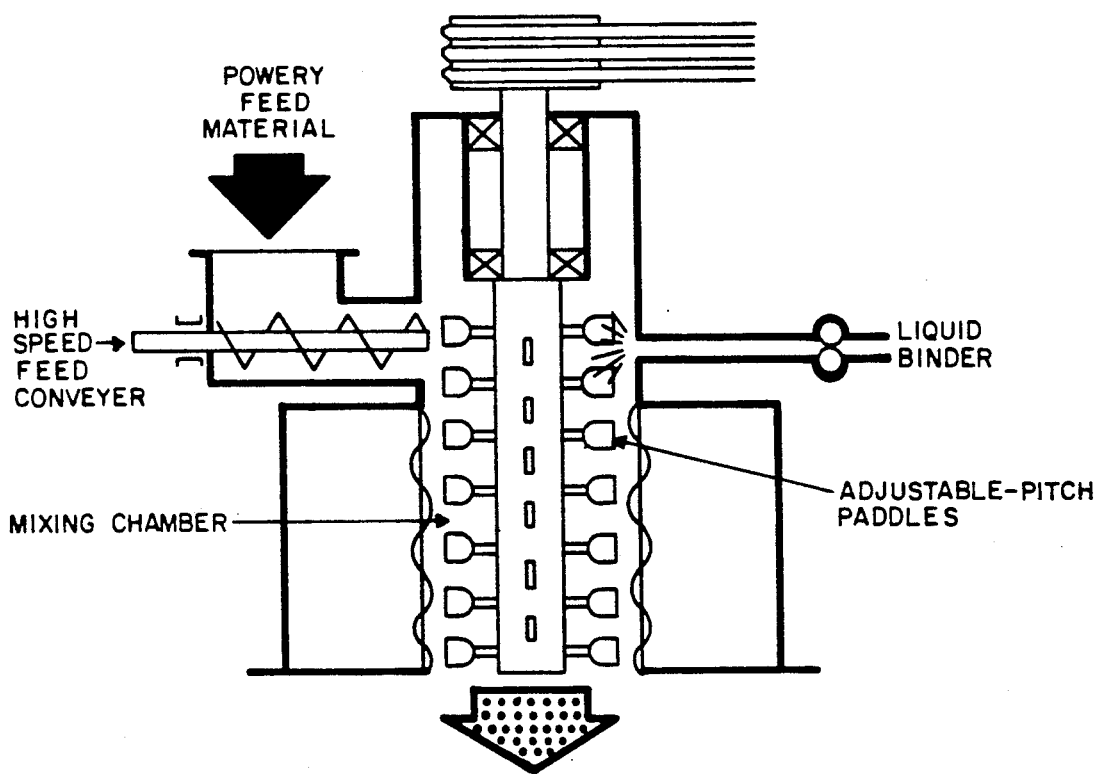

PROCESS FOR PRODUCING IMPROVED SUPERABSORBENT POLYMER AGGREGATES FROM FINES

This is a Continuation application of U.S. Ser. No. 203,368, filed May 31, 1988 now abandoned.

INTRODUCTION

Water-insoluble hydrogel-forming polymers are materials which are capable of absorbing large quantities of fluids such as water and body waste and which are further capable of retaining such absorbed fluids under moderate pressures. These absorption characteristics of such materials make them especially useful for incorporation into absorbent articles such as disposable diapers.

Frequently, hydroqel-forming absorbent materials comorise polymers of polymerizable unsaturated carboxylic acids or derivatives thereof, such as acrylic acid and/or alkali metal and alkyl acrylates. These polymers are rendered water-insoluble by cross-linking the carboxyl group-conlaining polymer chains using conventional cross-linking agents such as di- or poly-functional monomer materials. The degree of cross-linking in hydrogel and hydrogel-forming materials not only determines their water-solubility but is also an important factor in establishing two other characteristics of fluid absorbing hydrogels, i.e., absorbent capacity and gel strength. Absorbent capaclty oz "gel volume" is a measure of the amount of water or body fluid which a given amount of hydrogel-formirg material will absorb. Gel strength relates to the tendency of the hydrogel formed from such material to deform or "flow" under an applied stress.

For an overview of absorbent polymers of the type described above, reference is made to the references cited in U.S. Pat. No. 4,698,404 which cited references are specifically incorporated herein by reference.

While cross-linking agents may be used to prepare gel polymers as described above, it is possible to prepare acrylic acid gel polymers without utilizing cross-linking agents. Such products are described in U.S. Pat. No. 4,654,039, the disclosure of which is incorporated herein by reference.

Most absorbent gel polymers are normally polymerized in the form of an aqueous solution which produces hydrogel. This hydrogel is then usually dried and ground to a particle size most suitable for incorporation into absorbent products such as diapers, toweling and the like. The qrinding process tends to produce a percentaqe of fines which are small particles that cannot be utilized as such in the finished products souqht to be porduced from the gel polymers.

Another useful process for producing superabsorbent polymers is the batch, inverse suspension process. The main advantaqe of batch, inverse suspension products, such as described in the patents cited below, over gel products is the speed of absorotion. Increased speed is also one of the imorovements offered by the products resulting from this invention. The batch, inverse suspension technology is described in U.S. Pat. No. 4,340,706 with an improvement in such process heing further described in U.S. Pat. No. 4,698,404, the disclosures of which patents are incorporated herein by reference.

OBJECTS OF THE INVNETION

The invention has as one of its objects a method of utilizing acrylic acid gel polymer fines to produce an improved superabsorbent polymeric product.

Another object of the invention is to provide a treatment for the fines of an acrylic acid gel polymer made by conventional solution polymerization which fines are subsequently agglomerated to produce a polymeric superabsorbent prodùct having more rapid salt absorbency characteristics.

Other objects will be used here and after.

THE DRAWING

The drawing illustrates a commercial agglomerating device that may be used in the practice of the invention.

THE INVENTION

The invention comprises a method of making an improved water-absorbent polymer from absorbent acrylic acid gel polymer fines which have an average particle size less then about 500 microns which comprises agglomerating said particles with at least 0.05% by weight of a difunctional eooxide.

The Absorbent Acrylic Acid polymer Gel Fines

Acrylic acid polymer gel fines may result from any number of polymerization techniques but most often will occur using a solution pclymerization method such as, for instance, solution polymerization of partially neutralized acrylic acid. Other methods of producing acrylic acid polymers which result in gel fines usable in the practice of the invention are cited as references in the specification of U.S. Pat No. 4,654,039. While this patent describes the production of these polymers using laboratory scale equipment and methods, when such polymers are produced usinq large-scale crushing, mixing and grinding equipment, there are produced as an unwanted byproduct a substantial quantity of fines. These fines will vary in particle size depending upon the manufacturing process. This invention contemplates using polymer particle fines having an average particle size less than 500 microns. A preferred particle size range is less than about 250 microns. The acrylic acid gel polymers most useful in the practice of the invention contain from 50 to 99.999 mole percent of acrylic acid.

The agglomeration is conducted using at least 0.05%, preferahly between 0.1-2%, and most preferably between 0.2-0.8% by weight of difunctional epoxide which functions in conjunction with water as an agglomerating agent. Its main function, however, is to provide a cross-linking effect. Examples of the difunctional epoxides are ethylene glycol diglycidyl ether, 1,4-butanediol diglycidyl ether, (poly)-ethylene glycol diglycidyl ether, (poly)-propylene glycol diglycidyl ether, (poly-glycerin diglycidyl ether, and the like. Other difunctional epoxides are the haloepoxy compounds including, for instance, epichlorohydrin, α-methylepichlorohydrin and the like. Of the above materials, the diglycidyl ethers are preferred with ethylene glycol diglycidyl ether (EGDGE) being most preferred.

As indicated, the difunctional epoxide functions in the invention in its most preferred embodiment when water is the primary agglomerating agent. Depending upon the finished particle size sought, the amount of water added may vary between 1-20% and preferably 3-10% by weight. The amount of water added will determine the particle size of the finished aggregate. As a general rule, the greater amount of water the larger will be the aggregate.

To achieve optimum efficiency, the fines should be agglomerated to increase the particle size of the starting fines at least 2-5 times, and preferably 5-30 times.

Where the aggregates produced by the aggregation process are too large, they may be ground down to finer particle size without losing their absorptive properties. Where the aggregates produced by the process are still too small, they may be recycled back to the agglomerater for further aggregation.

Two different commercial acrylic acid absorbent polymer fines were agglomerated using a so-called Turboflex agglomerator manufactured by Bepex Corporation. This mixing device is generically described in the drawing.

Evaluations utilized the two commercial fines of acrylic acid superabsorbent polymer of the type illustrated in U.S. Pat. No. 4,654,039. The particle size distributions for Fine No. 1 and Fine No. 2 are shown below.

| | Particle Size Distribution of Starting Fines | | | | | |
|---|---|---|---|---|---|---|
| | Weight percent | | | | | |
| Sample | +70 Mesh | +100 Mesh | −70 + 200 Mesh | −100 + 200 Mesh | −200 + 325 Mesh | −325 Mesh |
| Fine No. 1 | | 0.24 | | 24.24 | 34.88 | 40.64 |
| Fine No. 2 | 0.08 | | 42.08 | | 39.84 | 18.00 |

These fines were agglomerated using the Turboflex mixer with the results being set forth below in Table I. Additional tests were run with the data being set forth in Table II.

TABLE I

Agglomeration Study at Bepex

| Test No. | Feed | Run Time (Mins) | Lbs/hr Feed | Second Binder | Wt % Water Added | Wt % Second Binder | Wt % +20 Mesh |
|---|---|---|---|---|---|---|---|
| 1 | No. 1 | 95 | 890 | | 5.60 | 0.00 | 4.9 |
| 2 | No. 1 | 24 | 890 | | 7.00 | 0.00 | 4.9 |
| 3 | No. 1 (−200 Mesh) | 12 | 890 | | 7.00 | 0.00 | 1.7 |
| 4 | No. 2 | 60 | 800 | | 7.80 | 0.00 | 12.5 |
| 5 | No. 2 | 30 | 800 | | 6.25 | 0.00 | 7.3 |
| 6 | No. 2 | 30 | 800 | | 8.85 | 0.00 | 16.7 |
| 7 | No. 1 | 60 | 960 | | 8.68 | 0.00 | 8.7 |
| 8 | No. 1 | 12 | 960 | PEG 600[4] | 6.83 | 0.87 | 4.5 |
| 9 | No. 1 | 16 | 960 | PEG 8000 | 6.06 | 0.78 | 3.3 |
| 10 | No. 1 | 9 | 960 | EGDGE | 8.97 | 0.23 | 5.1 |
| 11 | No. 2 | 10 | 990 | EGDGE | 7.78 | 0.20 | 7.0 |

| Test No. | Wt % −20 + 140 | Wt % −140 | Inlet[1] Dryer Temp | Dryer Bed Temp | Outlet Dryer Temp | IFX[2] Outlet % Water[3] | Final % Water |
|---|---|---|---|---|---|---|---|
| 1 | 65.6 | 29.5 | 201 | 135 | 133 | 9.5 | 4.9 |
| 2 | 71.2 | 23.9 | 199 | 130 | 123 | 10.4 | 6.4 |
| 3 | 57.6 | 40.7 | 202 | 149 | 141 | 10.5 | 5.3 |
| 4 | 66.1 | 21.4 | 194 | 133 | 130 | 14.8 | 6.6 |
| 5 | 66.1 | 26.6 | 199 | 143 | 136 | 13.9 | 6.1 |
| 6 | 57.0 | 26.3 | 200 | 153 | 409 | 13.6 | 5.8 |
| 7 | 64.0 | 27.3 | 205 | 155 | 128 | 11.4 | 4.5 |
| 8 | 57.9 | 37.7 | 195 | 127 | 124 | 9.5 | |
| 9 | 42.9 | 53.8 | 195 | 135 | 129 | 8.6 | |
| 10 | 39.6 | 55.4 | 177 | 133 | 118 | | |
| 11 | 53.0 | 40.0 | 186 | 133 | 126 | | |

[1]Dryer temperatures are the average for the three zones during the last 15 minutes of the run.
[2]Turboflex Aggregator
[3]Percent moistures are based on 3 hours at 105° C.
[4]Poly(ethylene glycol)

TABLE II

| Sample Number | Fines Source | Primary Binder | Second Binder | Wt % Water Added | Wt % Second Binder | Centrifuged[1] Capacity(g/g) | Lock-Up[2] (sec) | Vortex[3] Test(sec) |
|---|---|---|---|---|---|---|---|---|
| 1 | No. 1 | Water | | 5.6 | | 32.0 | 120 | 4.45 |
| 2 | No. 1 | Water | | 7.0 | | 32.3 | 120 | 4.33 |
| 3 | No. 1 | Water | | 7.0 | | 33.5 | 120 | 6.14 |
| 4 | No. 2 | Water | | 7.8 | | 41.0 | 90 | 5.7 |
| 5 | No. 2 | Water | | 6.25 | | 42.8 | 29.5 | 5.0 |
| 6 | No. 2 | Water | | 8.85 | | 41.6 | 37 | 5.52 |
| 7 | No. 1 | Water | | 8.68 | | 33.8 | 90 | 5.1 |
| 8 | No. 1 | Water | PEG 600 | 6.83 | 0.87 | 33.0 | 90 | 7.97 |
| 9 | No. 1 | Water | PEG 8000 | 6.06 | 0.78 | 33.0 | 90 | 5.22 |
| 10 | No. 1 | Water | EDGDE | 8.97 | 0.23 | 24.2 | 90 | 6.36 |

TABLE II-continued

| Sample Number | Fines Source | Primary Binder | Second Binder | Wt % Water Added | Wt % Second Binder | Centrifuged[1] Capacity(g/g) | Lock-Up[2] (sec) | Vortex[3] Test(sec) |
|---|---|---|---|---|---|---|---|---|
| 11 | No. 2 | Water | EDGDE | 7.78 | 0.2 | 29.7 | 14.2 | 3.65 |
| 12 | | | | | | | 13.0 | 3.56 |

[1] 0.9% saline
[2] Lock-Up Test = time required for 1 g of SA to absorb 30 g of 1.59% saline without mixing
[3] Vortex Test = time required for 50 g of 0.9% saline to lose vortex when 2 g of SA is added with stirring

Having thus described our invention, it is claimed:

1. A method of making an improved water-absorbent polymer from dried, crushed, and ground fines of absorbent acrylic acid gel polymers of the type capable of absorbing large quantities of fluid, and also containing from 50-99.999 mole percent of acrylic acid, which dried, crushed, and ground fines have an average particle size less than about 500 microns and which fines are obtained by drying, crushing, and grinding a polymer gel obtained from solution polymerization of acrylic acid and its salts, which method consists essentially of agglomerating said dried, crushed, and ground fines by adding thereto at least 0.05 percent by weight of a difunctional epoxide and from 1 to 20 percent of water, then mixing and reacting same with the fines, thereby agglomerating the fines to obtain an improved water absorbent agglomerated polymer having an increased particle size of from 5-30 times the size of the starting dried, crushed, and ground fines.

2. The method of claim 1 where the average particle size is less than about 100 microns.

3. The method of claim 1 where for difunctional epoxide is ethylene glycol diglycidyl ether.

* * * * *